United States Patent [19]

Casalnuovo et al.

[11] Patent Number: 5,484,902
[45] Date of Patent: Jan. 16, 1996

[54] ORGANOPHOSPHORUS SACCHARIDE NICKEL CATALYST

[75] Inventors: Albert L. Casalnuovo; Thaliyil V. Rajanbabu, both of Wilmington, Del.

[73] Assignee: E. I. Du Pont de Nemours and Company, Wilmington, Del.

[21] Appl. No.: 201,947

[22] Filed: Feb. 25, 1994

Related U.S. Application Data

[62] Division of Ser. No. 961,593, Oct. 15, 1992, Pat. No. 5,312,957, which is a division of Ser. No. 790,322, Nov. 12, 1991, Pat. No. 5,175,335.

[51] Int. Cl.$^6$ .......................... C07H 11/00; C07H 11/04; C07F 15/04
[52] U.S. Cl. .................. 536/18.4; 536/4.1; 556/146; 555/338
[58] Field of Search ............... 556/146; 536/4.1, 536/18.4; 558/338

[56] References Cited

U.S. PATENT DOCUMENTS

| | | | |
|---|---|---|---|
| 3,496,215 | 2/1970 | Drinkard et al. | 558/338 |
| 3,496,217 | 2/1970 | Drinkard et al. | 558/338 |
| 3,496,218 | 2/1970 | Drinkard, Jr. | 558/338 |
| 3,631,191 | 12/1971 | Kane et al. | 556/13 |
| 3,655,723 | 4/1972 | Drinkard, Jr. | 558/338 |
| 3,766,237 | 10/1973 | Chia et al. | 558/338 |
| 3,798,256 | 3/1974 | King et al. | 558/338 |
| 3,846,461 | 11/1974 | Shook, Jr. | 556/13 |
| 3,847,959 | 11/1974 | Shook, Jr. et al. | 556/13 |
| 3,873,594 | 3/1975 | Alvarez | 556/410 |
| 3,903,120 | 9/1975 | Shook, Jr. et al. | 556/13 |
| 3,925,445 | 12/1975 | King et al. | 558/338 |

FOREIGN PATENT DOCUMENTS 1417554  12/1975  United Kingdom.

OTHER PUBLICATIONS

W. Nugent et al., J. Org. Chem., 50:pp. 5370–5372 (1985).
C. Tolman et al., Adv. Catal., 33: pp. 1–46 (1985).
M. Hodgson et al., Organometallics, 7: pp. 1761–1766 (1988).
W. Jackson et al., J. Chem., 35:pp. 2069–2075 (1982).
M. Baker et al., J. Chem. Soc. Commun., p. 1292 (1991).
S. Harusawa et al., Synthetic Communications, 14(14) pp. 1365–1371 (1984).

*Primary Examiner*—Gary L. Kunz

[57] ABSTRACT

A composition for the enantioselective hydrocyanation of aromatic vinyl compounds comprising zero valent nickel and a chiral, nonracemic, bidentate organophosphorus ligand. The preferred organophosphorus ligand species is phenyl 2,3-bis-O-(3,5-bis(tri-fluoromethyl)phenyl)phosphino-4,6,0-benzilidene-B-D-glucopy-anoside as shown below.

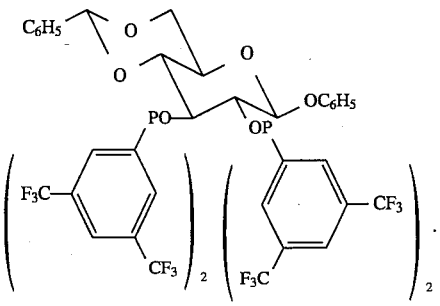

15 Claims, No Drawings

ORGANOPHOSPHORUS SACCHARIDE NICKEL CATALYST

This is a division of application Ser. No. 07/961,593, filed Oct. 15, 1992, now U.S. Pat. No. 5,312,957, a divisional of application Ser. No. 07/790,322 filed Nov. 12, 1991, now U.S. Pat. No. 5,175,335.

FIELD OF THE INVENTION

This invention relates to the enantioselective hydrocyanation of aromatic vinyl compounds to produce nonracemic mixtures of chiral arylpropionitriles; to novel catalyst compositions used therein which are comprised of zero-valent nickel and chiral, nonracemic carbohydrate phosphorus ligands; and to optically pure (S)-(−)-2-(6-methoxy-2-naphthalene)propionitrile which is produced using the novel process and catalyst compositions.

BACKGROUND OF THE INVENTION

Arylpropionitriles are useful precursors to an important class of chiral arylpropionic acids that are nonsteroidal, antiinflammatory drugs, *Tetrahedron,* 1986, 42 (15), 4095, *J. Org. Chem.,* 1985, 50, 5370. In most cases, the beneficial properties of these drugs are believed to arise from only one enantiomer and, in some cases, the properties of the other enantiomer are harmful. Thus selective, synthetic routes to nonracemic mixtures of arylpropionitriles or arylpropionic acids are highly desirable.

U.S. Pat. Nos. 3,496,215; 3,496,217; 3,496,218; 3,631,191; 3,655,723; 3,798,256; 3,846,461; 3,847,959; and 3,903,120 describe nonenantioselective alkene hydrocyanation in the presence of low valent, organophosphorous Ni catalysts and, in some cases, Lewis acid promoters. The nickel-catalyzed hydrocyanation of styrene and vinylnapthalene derivatives occurs in a predominantly Markovnikov fashion to generate racemic mixtures of chiral, arylpropionitriles (*J. Org. Chem.,* 1985, 50, 5370; *Adv. Catal.,* 1985, 33, 25–31).

Very few examples of enantioselective, transition-metal-catalyzed alkene hydrocyanations have been documented. Reported enantioselective inductions pertain primarily to the enantioselective hydrocyanation of norbornene derivatives, and only modest product e.e.'s (enantiomeric excesses) have been obtained. The highest e.e. reported for any transition-metal-catalyzed enantioselective alkene hydrocyanation is 40% for a Pd catalyzed hydrocyanation of norbornene (6% product yield; *Organometallics* 1988, 7, 1761).

To achieve the enantioselective alkene hydrocyanation of the instant invention, Applicants have used a class of nickel hydrocyanation catalyst compositions comprised of zero-valent nickel and chiral, nonracemic bidentate organophosphorus ligands. Such catalysts are not known to have been used previously in enantioselective hydrocyanation of aromatic vinyl compounds.

The use of catalyst compositions of zero-valent nickel and chiral, nonracemic O-substituted, bidentate diolphosphorus ligands derived from chiral diols for the enantioselective hydrocyanation of norbornene have been reported in Aust. J. Chem., 19082, 35, 2069; J. Chem. Soc. Commun., 1991, 1292). However, use of such catalysts on aromatic vinyl substrates is not disclosed.

Nonracemic mixtures of chiral, O-substituted diolphosphorus ligands derived from carbohydrates, such as D-glucose, have been used previously as ligands in the catalytic, enantioselective hydrogenation of α,β-unsaturated acid derivatives. The catalyst compositions of the instant invention, however, which comprise nickel, are not known in the enantioselective hydrocyanation of alkenes.

In addition, the preparation of racemic 2-(6-methoxy-2-naphthalene)propionitrile has been previously reported in Synthetic Commun. 1984, 14, 1365; J. Org. Chem. 1985, 50, 5370, but the preparation of the pure S enantiomer is not disclosed. Using a preferred embodiment of the process of the invention Applicants have achieved the preparation of optically pure (S)-(−)-2-(6-methoxy-2-naphthalene)propionitrile.

SUMMARY OF THE INVENTION

Applicants' invention encompasses 1) a process for enantioselective hydrocyanation of aromatic vinyl compounds wherein nonracemic mixtures of chiral, arylpropionitriles are produced, 2) novel catalyst compositions which are used in the process, and 3) an optically pure product of the process: (S)-(−)-2-(6-methoxy-2-naphthalene)propionitrile.

The invention provides a process for enantioselective hydrocyanation comprising:

reacting an aromatic vinyl compound of the formula

Ar—CH=CH$_2$ wherein Ar is an aromatic or heteroaromatic radical which each may additionally be substituted with halogen, ether, ester, alcohol, amide or ketone groups;

with a source of HCN;

in the presence of a catalyst composition comprising zero-valent nickel and a chiral, nonracemic, bidentate organophosphorus ligand of the formula

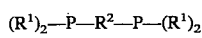

$(R^1)_2$—P—$R^2$—P—$(R^1)_2$ wherein each $R^1$ is independently a $C_1$ to $C_{20}$ hydrocarbyl, alkoxy, or aryloxy, each optionally substituted with one or more halogen, alkyl halide, ether, ester, carboxy or amide groups; and $R^2$ is a hydrocarbyl or hydrocarbyloxy, each optionally substituted with one or more halogen, ether, ester, alcohol, amide or ketone groups, or $R^2$ is a $C_4$ to $C_{40}$ carbohydrate, optionally substituted with one or more hydrocarbyl, halogen, ether, ester, alcohol, amide or ketone groups;

to produce a nonracemic nitrile product of the formula

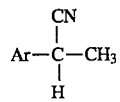

wherein Ar is defined as above.

The invention further provides a catalyst composition comprising a source of zero-valent nickel and a chiral, nonracemic, bidentate organophosphorus ligand of the formula

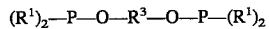

$(R^1)_2$—P—O—$R^3$—O—P—$(R^1)_2$ wherein each $R^1$ is independently a $C_1$ to $C_{20}$ hydrocarbyl, alkoxy or aryloxy, each optionally substituted with one or more alkyl, cycloalkyl, alkenyl, aralkyl, aryl, halogen, ether, ester, carboxy or amide groups; and $R^3$ is a $C_4$ to $C_{40}$ dideoxycarbohydrate, optionally substituted with one or more hydrocarbyl, halogen, ether ester, alcohol, amide or ketone groups.

The invention further provides optically pure (S)-(-)-2-(6-methoxy-2-naphthalene)propionitrile.

DETAILED DESCRIPTION OF THE INVENTION

The process of the instant invention, whereby enantioselective hydrocyanation is accomplished on aromatic vinyl compounds, is useful, for example, to produce any of a class of arylpropionitriles which are precursors to nonsteroidal, anti-inflammatory drugs such as ibuprofen and naproxen. The novel catalyst compositions of the instant invention, comprising zero-valent nickel and chiral, nonracemic diolphosphorus ligands derived from carbohydrate diols, are useful for accomplishing the above-described enantioselective hydrocyanation reactions. Optically pure (S)-(-)-2-(6-methoxy-2-naphthalene)propionitrile is a valuable precursor to the nonsteroidal, antiinflammatory drug (S)-(-)-2-(6-methoxy-2-naphthalene)propionic acid (naproxen).

By the term "carbohydrate", Applicants mean the class of organic compounds comprising the general formula $(C.H_2O)_n$, wherein n is equal to or greater than four. The carbohydrate-derived ligands of the invention are derived from $C_4$ to $C_{40}$ carbohydrates including monosaccharides, disaccharides and oligosaccharides.

By the term "heteroaromatic", Applicants mean a cyclic aromatic compound containing at least one oxygen, nitrogen or sulfur atom in the ring.

By the term "hydrocarbyl", Applicants include all alkyl, aryl, aralkyl or alkylaryl carbon substituents, either straight-chained, cyclic, or branched.

By the term "substituted hydrocarbyl, substituted alkoxy, or substituted aryloxy", Applicants refer to a structure which is substituted with one or more of the following groups: alkyl, cycloalkyl, alkenyl, aralkyl, aryl, halogen, alkyl halide, ether, ester, carboxy, and amide.

By the term "hydrocarbyloxy", Applicants describe the group —O—R—O—; wherein R is a hydrocarbyl.

In describing a carbohydrate group of the formula O—R—O, the group R is named by using the prefix "dideoxy" with the name of the parent diol of the formula HO—R—OH. For example, the name 2,3-dideoxyglucose refers to the group:

and accordingly, the corresponding carbohydrate group O—R—O is:

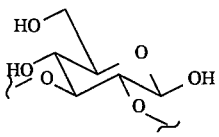

The suffix -ose- when used in combination with carbohydrate root names, shall include those compounds wherein the OH groups are protected as ethers or esters. By this definition, for example, the glucopyranoside structure shown below is termed "a glucose"

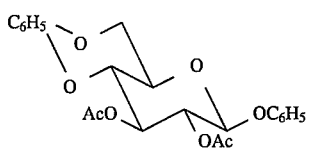

wherein Ac is an acetyl.

By the term "substituted styrene", Applicants refer to a styrene molecule which is substituted with at least one of the following groups: alkyl, cycloalkyl, alkenyl, aralkyl, aryl, halogen, ether, ester, carboxy, amine, and amide.

By the term "chiral", Applicants mean "existing as a pair of enantiomers". These stereoisomers, designated the R and S isomers, are nonsuperimposable mirror images of one another. A chiral material may either contain an equal amount of the R and S isomers in which case it is called "racemic" or it may contain inequivalent amounts of R and S isomer in which case it is called "optically active", or "nonracemic".

By the term "enantiomeric excess" ("ee"), Applicants mean the absolute difference between the percent of R enantiomer and the percent of S enantiomer of an optically active compound. For example, a compound which contains 75% S isomer and 25% R isomer will have an enantiomeric excess of 50%.

The term "optically pure" refers to an enantiomeric excess greater than 99%.

By the term "enantioselective" Applicants mean the ability to produce a product in an optically active form.

The enantioselective hydrocyanation reaction of the invention is carried out, either as a batch, semi-batch or continuous process, by the addition of a source of HCN to an aromatic vinyl compound of the formula Ar—CH=CH$_2$. The reaction is carried out in the presence of a chiral, nonracemic, nickel hydrocyanation catalyst composition to produce chiral, nonracemic, arylpropionitriles of the formula Ar—CH(CN)CH$_3$.

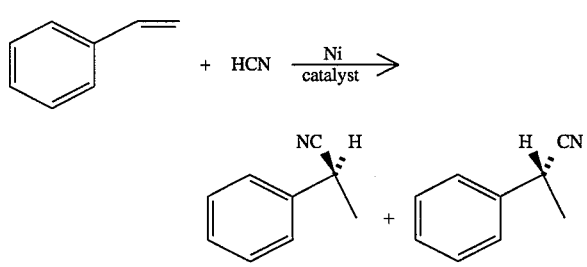

The substrates of the invention, described by the formula Ar—CH=CH$_2$, may be any aromatic or heteroaromatic compound with a vinyl functional group, which is represented by —CH=CH$_2$. Examples of Ar include, but are not limited to, phenyl, naphthyl and methoxynaphthyl. Representative examples of substrates used in the invention include, but are not limited to, 2-vinylnaphthalene, 6-methoxy-2-vinylnaphthalene, 4-isobutylstyrene and styrene. Further, Applicants contemplate that the process of the instant invention may effectively achieve enantioselective hydrocyanation of conjugated alkenes, as well as the aromatic vinyl compounds of the present invention.

The aromatic vinyl substrates of the invention may be made by methods which are well-known in the art e.g., Organometallics, 1991, 10, 1183–1189 which is hereby incorporated by reference; and some of these substrates are available commercially as well.

For all embodiments of the Applicants' invention the chiral, nonracemic, nickel hydrocyanation catalyst comprises a chiral, nonracemic, organophosphorus ligand and a source of zero-valent nickel. The zero-valent nickel can be prepared or generated according to techniques well-known in the art (U.S. Pat. Nos. 3,496,217; 3,631,191; 3,846,461; 3,847,959; and 3,903,120 which are incorporated by reference). Zero-valent nickel compounds that contain ligands which can be displaced by the chiral organophosphorus ligand are a preferred source of zero-valent nickel. Two such preferred zerovalent nickel compounds are Ni(COD)2 (COD is 1,5-cyclooctadiene) and Ni(P(O-o-$C_6H_4CH_3)_3)_2(C_2H_4)$, both of which are known in the art. Alternatively, divalent nickel compounds may be combined with a reducing agent, and are then able to serve as suitable sources of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

The catalyst composition of the invention also comprises, in addition to the nickel, a chiral, nonracemic, bidentate organophosphorus ligand of the formula $(R^1)_2P—R^2—P(R^1)_2$ wherein each $R^1$ may independently be a $C_1$ to $C_{20}$ hydrocarbyl, alkoxy, or aryloxy, each optionally substituted and $R^2$ may be a $C_1$ to $C_{40}$ hydrocarbyl or $C_1–C_{40}$ hydrocarbyloxy, each optionally substituted with one or more halogen, ether, ester, alcohol, amide or ketone groups, or $R^2$ is a $C_4$ to $C_{40}$ carbohydrate, optionally substituted with hydrocarbyl, halogen, ether, ester, alcohol, amide or ketone groups. The preparations of such chiral organophosphorus ligands are generally known in the art and many of these ligands are commercially available.

In a more particular embodiment, the process of the invention employs a ligand comprising a chiral, nonracemic O-substituted diolphosphorus of the formula $(R^1)_2P—R^2—P—(R^1)_2$ wherein $R^1$ is defined as above, and $R^2$ is a moiety of the formula —O—$R^3$—O—, wherein $R^3$ is $C_1$ to $C_{40}$ hydrocarbyl or $C_4$ to $C_{40}$ dideoxycarbohydrate, each optionally substituted with one or more hydrocarbyl, halogen, ether, ester, alcohol, amide or ketone groups; and such that the fragment of the ligand defined by the structure PO—$R^3$—OP is chiral. By this definition Applicants intend that the chirality of the O-substituted diolphosphorus ligand arise from the chirality of the parent diol HO—$R^3$—OH. Ligands of this embodiment of the invention include ligands derived from carbohydrates (discussed below), tartrate esters, 2-2'-binaphthols, and terpene diols. Most preferred of the noncarbohydrate diols is diisopropyltartrate.

In the preferred embodiment, the chirality of the chiral, nonracemic O-substituted diolphosphorus ligand $(R^1)_2P—R^2—P(R^1)_2$ is derived from a carbohydrate diol. Specifically, in this preferred embodiment, the process is carried out by employing chiral, nonracemic, O-substituted carbohydrate phosphorus ligands; including particularly pyranose, furanose, disaccharide and oligosaccharide organophosphorus ligands. Examples are represented by the formulas I–IV,

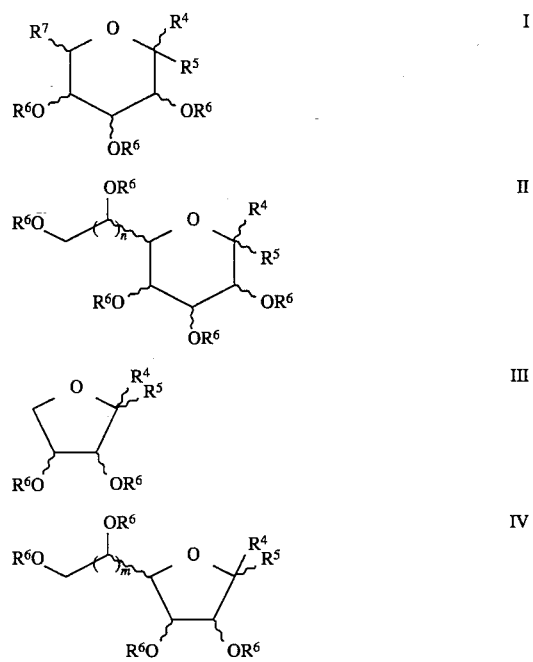

wherein:

n=0–2;

m=0–3;

$R^4$ groups are independently H, hydroxy, $C_1$ to $C_{20}$ hydrocarbyl, alkoxy, aryloxy, O-substituted pyranose or O-substituted furanose;

$R^5$ groups are independently H, hydroxymethyl ($CH_2OH$), alkoxymethyl, aryloxymethyl, or $CH_2OP(X)_2$ where X is aryl, alkoxy, or aryloxy;

$R^6$ groups are independently H, $C_1$ to $C_{20}$ hydrocarbyl, acyl, or $P(X)_2$ where X is aryl, alkoxy, or aryloxy;

$R^7$ is H or $CH_3$;

and the sum total of $P(X)_2$ groups present in the O-substituted pyranose, furanose, dissacharide or oligosaccharide orgenophosphorus ligand is equal to 2.

Applicants also specifically include within the carbohydrate ligand compositions of the invention those carbohydrates containing protective groups. By the term "protective group", Applicants include groups such as ethers and esters which may function to provide chiral recognition of the sugar molecule, and further are commonly employed to protect the sugar molecule from nonselective reactions. Applicants further intend to particularly include disaccharides formed by Joining two of the structures shown in formulas I–IV through an oxygen atom at the anomeric position of the furanose or pyranose ring. Two examples of such dissacharides are shown below wherein Ph is phenyl and Ac is acetyl.

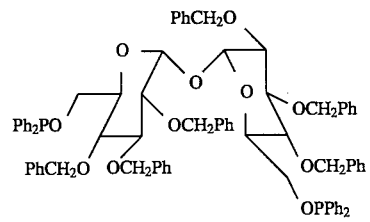

-continued

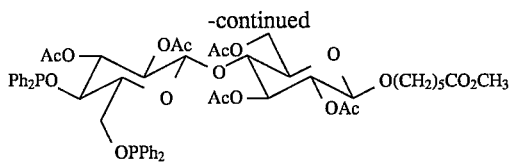

Most preferably, the chiral, nonracemic, organophosphorus ligand is a chiral, nonracemic, O-substituted glucopyranose organophosphorus ligand of the formula V,

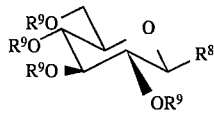

wherein:
- $R^8$ is H, hydroxy, $C_1$ to $C_{20}$ hydrocarbyl, alkoxy, or aryloxy;
- $R^9$ is independently selected from H, $C_1$ to $C_{20}$ hydrocarbyl, acyl or $P(X)_2$, where X is aryl, alkoxy, aryloxy;
- and the sum total of $P(X)_2$ groups present in the O-substituted glucopyranose organophosphorus ligand is equal to 2.

Chiral, nonracemic O-substituted diolphosphorus ligands, including carbohydrate derived diolphosphorus ligands, can be prepared according to techniques well-known in the art. (*J. Organomet. Chem.*, 1978, 159, C29; *Tetrahedron Lett.*, 1978, 1635; *J. Org. Chem.*, 1980, 45, 62; *Bull. Chem. Soc. Jpn.*, 1986, 59, 175; *J. Mol. Catal.*, 1986, 37, 213; *J. Prakt. Chem.*, 1987, 329 (4), 717). In general, diol derivatives containing unprotected hydroxyl groups are treated with a $P(R)_2Cl$ (wherein R may generally be an alkyl, aryl, alkoxy, or aryloxy) reagent in the presence of a base, such as pyridine or triethylamine, to produce the desired phosphinite or phosphite. Some $P(R)_2Cl$ reagents are commercially available, such as $PPh_2Cl$ (Ph=phenyl). $P(R)_2Cl$ reagents, where R=aryl or alkyl, can also be prepared in two steps by treatment of readily available dialkyl phosphites, such as dibutyl phosphite, $HP(O)(O)_2$, with RMgBr followed by treatment of the resulting $HP(O)R_2$ product with $PCl_3$ (*J. Am. Chem. Soc.*, 1951, 73, 4101; *J. Am. Chem. Soc.*, 1952, 74, 5418; *J. Org. Chem.*, 1966, 31, 1206). $P(R)_2Cl$ reagents, where R=alkoxy or aryloxy, can be prepared in two steps by treatment of $P(NEt_2)_3$ with ROH to generate $P(OR)_2(NEt_2)$, followed by treatment with $CH_3COCl$ to generate $P(OR)_2Cl$. Illustrative preparations are provided below.

For all embodiments of the invention the chiral, nonracemic nickel hydrocyanation catalyst may be prepared by mixing the zero-valent nickel source and the chiral, nonracemic, organophosphorus ligand, preferably in a nonpolar organic solvent such as benzene, toluene or hexane, under an inert atmosphere such as $N_2$ or Ar in a temperature range from 0° C. to 120° C., preferably in a temperature range from 0° C. to 80° C., and then adding the mixture to the aromatic vinyl compound. Alternatively, the hydrocyanation catalyst may be prepared in situ by adding the zero-valent nickel source and the chiral, nonracemic, organophosphorus ligand directly into the reaction mixture containing the aromatic vinyl compound.

The molar ratio of chiral, nonracemic, organophosphorus ligand to nickel may vary between 0.01:1 to 10:1, preferably between 1:1 to 2:1, most preferably between 1:1 to 1.5:1.

The molar ratio of nickel to aromatic vinyl compound may vary between 0.0001:1 to 1:1, preferably between 0.001:1 to 0.05:1.

The aromatic vinyl compound starting material, which is represented by the formula Ar—CH=CH$_2$ may be dissolved in any organic solvent compatible with the reagents employed, preferably a nonpolar solvent such as, but not limited to, benzene, toluene, or hexane. Alternatively, for liquid aromatic vinyl compounds, HCN may be added directly to the mixture of catalyst and aromatic vinyl compound.

HCN may be added as a pure compound or as a solution in any organic solvent compatible with the reagents employed, preferably a nonpolar solvent such as benzene, toluene or hexane. Alternatively HCN may be generated in situ (e.g. from cyanide salts or cyanohydrins). The amount of HCN added to the reaction process may vary from 0.01 to 10.0 molar equivalents per equivalent of the aromatic vinyl group. A minimum of 1.0 equivalent of HCN is required to obtain complete conversion of the vinyl equivalents in the substrate.

The hydrocyanation reaction is carried out over a temperature range from 20° to 120° C., preferably 25° to 80° C., under an inert atmosphere such as $N_2$ or Ar.

The Applicants note that the observed e.e.'s generally decrease as the temperature is increased.

The enantioselective hydrocyanation reactions are generally complete within 1–48 hours of the final HCN addition.

The preparation of optically pure (S)-(−)-2-(6-methoxy-2-naphthalene)propionitrile is achieved using a preferred embodiment of the process for the enantioselective hydrocyanation of an aromatic vinyl compound using a catalyst composition comprising zero-valent nickel and a chiral, nonracemic, bidentate organophosphorus Ligand of the formula $(R^1)_2P—R^2—P(R^1)_2$ wherein the aromatic vinyl compound is 6-methoxy-2-vinylnaphthalene, the preferred source of zero-valent nickel is $Ni(COD)_2$, $R^1$ is the aryl group 3,5-bis(trifluoromethyl)phenyl, and $R^2$ is the O-substituted β-D-glucopyranose derivative of the formula VI

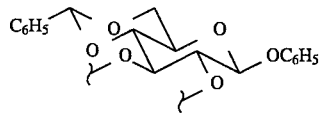

For the preparation of optically pure (S)-(−)-2-(6-methoxy-2-naphthalene)propionitrile, the enantioselective hydrocyanation is preferably carried out at 25° C. under a $N_2$ atmosphere using 1 to 2 molar equivalents of HCN per molar equivalent of 6-methoxy-2-vinylnaphthalene. HCN is preferably dissolved in a non-polar organic solvent such as toluene or benzene and added to a mixture of the zero-valent nickel, chiral, nonracemic, bidentate organophosphorus ligand and 6-methoxy-2-vinylnaphthalene in a non-polar organic solvent such as benzene, toluene or hexane. In this preferred embodiment a molar ratio between 0.005:1 to 0.05:1 of nickel to aromatic vinyl compound is preferred. A molar ratio between 1:1 to 1:2 of nickel to organophosphorus ligand is preferred.

Using these preferred conditions an e.e. between 75–85% of the S enantiomer of 2-(6-methoxy-2-naphthalene)propionitrile and a yield between 75–100% will generally be obtained. Isolation of the product nitrile can be achieved by flash column chromotagraphy of the reaction mixture on silica gel using 10% diethyl ether/hexane as eluent. Alternatively, product nitrile may precipitate from the reaction mixture. Optically pure (S)-(−)-2-(6-methoxy-2-naphthalene)propionitrile may then be obtained by one or two recrystallizations from an organic solvent or a mixture of organic solvents, preferably diethyl ether/hexane mixtures. Optically pure (S)-(−)-2-(6-methoxy-2-naphthalene)propionitrile is readily distinguished from the racemic nitrile by its melting point (99°–100° C. as compared to 72°–74° C. for racemic nitrile) and optical rotation ([α]$_D^{25}$=−28.4°±1.6° C. 0.5 in CHCl$_3$)

Procedures for the Preparation of Chiral, O-Substituted Carbohydrate Phosphinite and Phosphite Ligands The following procedures illustrate the preparation of the chiral ligands. All reactions were carried out under a N$_2$ atmosphere using standard Schlenk techniques or a Vacuum Atmospheres Co. Drybox. With the exception of compound 1, all isolated compounds were handled and stored under a N$_2$ atmosphere. Solvents were distilled and degassed prior to use.

Preparation of Bis(3,5-bis(trifluoromethyl)-phenyl)phosphine oxide (3,5-(CF$_3$)$_2$C$_6$H$_3$)$_2$P(O) H, Compound 1

A solution of dibutylphosphite, HP(O)(OBu)$_2$ (0.025 mol, 4.855g), in 5 ml of Et$_2$O was added dropwise by an addition funnel to a slurry of KH (0.0275 mol, 1.103 g) in 10 ml of Et$_2$O (caution: H$_2$ evolution occurs) and stirred for 5 hours at room temperature. The reaction mixture was filtered to remove excess KH and washed with Et$_2$O. The resulting filtrate of KP(O)(OBu)$_2$ was treated dropwise with a solution of (3,5-(CF$_3$)$_2$C$_6$H$_3$)MgBr (0.050 mol) in about 15 ml of Et$_2$O. The reaction mixture was stirred for 4 hours, quenched with 50% aqueous Na$_2$HPO$_4$, filtered and rinsed with Et$_2$O. The organic layer was separated and the aqueous layer extracted twice with Et$_2$O. The organic layers were combined, dried over Na$_2$SO$_4$, filtered and then concentrated to dryness in vacuo. The resulting dark solids were refluxed briefly in benzene, the mother liquor filtered to remove dark solids, and the filtrate concentrated to dryness in vacuo to give 8.72 g (74%) of the desire phosphine oxide. $^{31}$P {$^1$H} (C$_6$D$_6$): 12.1 ppm, s (JPH=506 Hz, $^1$H coupled spectrum). $^1$H (C$_6$D$_6$): 7.27, d, 509 Hz, 1H; 7.56, s, 2H; 7.78, d, 13.0 Hz, 4H.

Preparation of Bis (3,5-bis(trifluoromethyl)phenyl)phosphine Chloride (3,5-(CF$_3$)$_2$C$_6$H$_3$)$_2$PCl, Compound 2

PCl$_3$ (3.49 g, 0.0255 mol) was added dropwise to a solution of (3,5-(CF$_3$)$_2$C$_6$H$_3$)$_2$P(O)H,1, (8.72 g, 0.018 mol) in about 35 ml of CH$_2$Cl$_2$ and stirred at room temperature for about 1.5 hours. The reaction mixture was concentrated to an oil under high vacuum at room temperature, and then the product was vacuum transferred from the nonvolatile byproducts under high vacuum by heating with a heat gun. Yield 6.36 g (72%) of a white solid of about 95 mol % purity by $^{31}$P and $^1$H NMR spectroscopy. $^{31}$P{$^1$H} (C$_6$D$_6$): 70.4, s. $^1$H (C$_6$D$_6$): 7.54, s, 1H; 7.66, d, 6.5 Hz.

Preparation of Phenyl 2,3-bis-O-(3,5-bis(trifluoromethyl)phenyl)phosphino-4,6-O-benzylidene-β-D-glucopyranoside, Compound 3

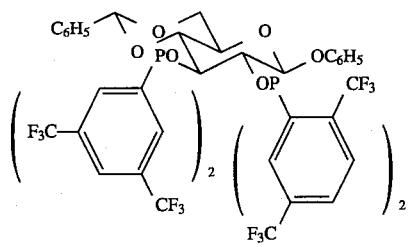

A solution of (3,5-(CF$_3$)$_2$C$_6$H$_3$)$_2$PCl, 2 (1.558 g, 3.15 mmol) in about 3 ml of Et$_2$O was cooled to about 0° C. and then added dropwise to a slurry, previously cooled to about 0° C., of NEt$_3$ (0.506 g, 5.0 mol) and phenyl 4,6-O-benzylidene-β-D-glucopyranoside in about 15 ml of Et$_2$O.

The reaction mixture was stirred for about 1.5 hours at room temperature, filtered to remove HNEt$_3$Cl, the solids washed with Et$_2$O, and the filtrate concentrated to dryness in vacuo. The filtrate residue was then slurried with about 20 ml of hexane for about 16 hours. The resulting white solids were collected by filtration and dried in vacuo. Yield 1.36 g (88%). $^{31}$P{$^1$H} (C$_6$D$_6$): 108.4, s, 1P; 107.5, s, 1P. 1H (C$_6$D$_6$): 2.980, m, 1H; 3.149, t, 9.2 Hz, 1H; 3.272, t, 10.2 Hz, 1H; 3.884, d.d., 4.9, 10.4 Hz, 1H; 4.186, m, 2H; 4.690, m, 1H; 4.936, s, 1H; 6.327, d, 7.9 Hz, 2H; 6.69, t, 7.3 Hz, 1H; 6.875, t, 8.0 Hz, 2H; 6.968, m, 2H; 7.049, m, 3H; 7.353, s, 2H; 7.388, s, 2H; 7.818, m, 8H.

Preparation of (S,S)-1,2-diphenyl-1,2-O-(N,N-diethylaminophosphino)ethane, Compound 4

A solution of P(NEt$_2$)$_3$ (0.371 g, 1.5 mol) in about 1 ml of benzene was added to a solution of (S,S)-hydrobenzoin (0.321 g, 1.5 mmol) in about 5 ml of benzene and then refluxed for 3 hours under N$_2$. $^{31}$p NMR analysis indicated essentially complete conversion to the desired product. $^{31}$P{$^1$} (C$_6$D$_6$): 150.5, s.

Preparation of (S,S)-1,2-diphenyl-1,2-O-(chlorophosphino)ethane, Compound 5

The sample of 4 prepared as described above was concentrated in vacuo to an oil, dissolved in about 5 ml of CH$_2$Cl$_2$, and treated dropwise with a solution of acetyl chloride (0.130 g, 1.65 mmol) in about 1 ml of CH$_2$Cl$_2$. After 4 hours of stirring the sample was concentrated to dryness under high vacuum. $^{31}$P{$^1$H} (C$_6$D$_6$): 173.2, s.

Preparation of Phenyl 2,3-bis-O-(((S,S)-1',2'-diphenyl-1',2'-O-phosphino)ethane)-4,6 -O-benzylidene-β-D-glucopyranoside. Compound 6 (Ligand A for Examples 16 and 17)

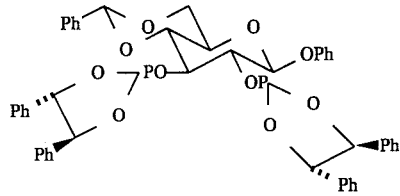

A solution of 5 in about 5 ml of CH$_2$Cl$_2$, previously cooled to about 0° C., was added dropwise to to a solution of phenyl 4,6-O-benzylidene-β-D-glucopyranoside (0.234 g, 0.68 mmol), and 4-dimethylaminopyridine (0.018 g, 0.15 mmol) in about 15 ml of pyridine/CH$_2$Cl$_2$ (50/50 by volume), previously cooled to about 0° C. The reaction mixture was stirred for about 16 hours and concentrated to dryness in vacuo. The residue was refluxed in hot benzene, filtered to remove hydrochloride salts, and the filtrate concentrated to dryness in vacuo. The residue was slurried in hexane and the resulting white solids were filtered, washed with hexane and dried in vacuo. Yield 0.549 g (97%). $^{31}$P{$^1$H} (C$_6$D$_6$): 143.4, s, 1P; 144.9, s, 1P. $^1$H (C$_6$D$_6$): 3.09, m, 1H; 3.35, t, 9.7 Hz, 2H; 4.00, d.d.,1H; 4.52, q., 1H; 4.64, q., 1H; 4.80, m., 3H; 5.12, s, 1H; 5.22, d., 9.3 Hz, 1H; 5.40, d., 9.3 Hz, 1H; 6.72, t., 1H; 6.8–7.3, m., 23H; 7.40, d., 7.2 Hz, 2H; 7.46, d., 7.2Hz, 2H; 7.67, d.d., 1.9, 7.5 Hz, 2H.

Ligands B through J were made using similar procedures to those described above, or were obtained commercially.

Preparation of [(C$_6$H$_5$)$_2$P]$_2$ -(R)-(+)-1,1'-binaphtholate (BINAP)

A glass reactor is charged with (R)-(+)-1,1' -binaphthol (1.00 g), triethylamine (3.25 cc), and anhydrous diethylether (15 cc) and cooled under nitrogen atmosphere to −78° C. (dry ice/acetone bath). A solution of diphenylphosphorus chloride (Ph$_2$PCl) (1.25 cc) in diethyl ether (10 cc) is added dropwise with stirring. The resulting suspensions is allowed to warm to room temperature and stirring continued overnight. The mixture is filtered and the filtrate evaporated to dryness under vacuum. The resulting white powder was washed with pentane to give the titled compound, a free flowing white powder (1.58 g; 69% yield) which was dried under high vacuum and submitted for element carbon and hydrogen analysis. Calc'd for $C_{44}H_{32}O_2P_2$ (MW 654); % C 80.73; % H 4.89. Found % C 81.15, 80.87; % H 4.82, 4.63; % N 0.03, 0.01.

In a similar manner, chelating ligands were made from dimethyl-D-tartrate, dimethyl-L-tartrate, diisopropyl-D-tartrate, and (+)-Pinanediol.

EXAMPLES

Enantioselective Hydrocyanation of Vinyl Aromatic Compounds for Examples 1–36

Results and reaction conditions for the enantioselective hydrocyanation of vinyl aromatic compounds are shown in Tables 1, 2 and 3, except for Examples 37, 46 and 47, which are described therein. With a few exceptions which are noted, the hydrocyanations were carried out by the dropwise addition of a toluene solution of HCN (typically 0.05 to 0.15 equivalents of HCN per equivalent of vinyl aromatic compound) to a benzene or toluene solution of $Ni(COD)_2$ (COD=1,5-cyclooctadiene), the chiral ligand and the vinyl aromatic compound under a $N_2$ atmosphere. Conversions were determined by GC using a cross-linked methylsilicone capillary column (30 m×0.530 m). E.E.'s were determined by HPLC using a Bakerbond Chiral DNBPG, Chiralcel OJ or OB column: 5% i-PrOH/Hexane, 1 ml/min., 40° C. HPLC samples were passed through a short pad of silica gel and eluted with 90/10 hexane/$Et_2O$ prior to analysis. Positive e.e. values indicate an excess of the earlier eluting enantiomer; Negative values indicate an excess of the later eluting enantiomer. For examples involving 2-vinylnaphthalene (VN) and 6-methoxy-2-vinylnaphthalene (MVN) the earlier (+) enantiomer was determined to be the S enantiomer by comparison to a sample enriched in the "S" enantiomer. This enriched sample was obtained by conversion of commercially available, optically pure S-(+)-2-(6-methoxy-2-naphthalene)propionic acid (Naproxen) into the corresponding amide with $ClO_2Et/NH_3$ in $CHCl_3$, followed by conversion to the nitrile with $Ph_3/CCl_4$ in dichloroethane. The relative assignments of the enantiomers derived from styrene and 4-isobutylstyrene were not determined.

Procedure I

A solution of $Ni(COD)_2$ (0.009 g, 0.033 mmol) in about 1 ml of benzene was added to a solution of the chiral ligand (0.042 mmol) in about 1 ml of benzene, stirred for 30 minutes and added to the vinyl aromatic compound (0.65 mmol). The reaction mixture was brought to the specified temperature and HCN (0.600 ml, 0.22M in toluene, 0.132 mmol) was added by syringe or autopipette. The reaction mixture was analyzed by GC and HPLC after about 3–4 hours of stirring.

Procedure II

A solution of $Ni(COD)_2$ (0.009 g, 0.033 mmol) in about 1 ml of benzene was added to a solution of the chiral ligand (0.066 mmol) in about 1 ml of benzene, stirred for 30 minutes and added to the vinyl aromatic compound (0.65 mmol). The reaction mixture was brought to the specified temperature and HCN (0.600 ml, 0.22M in toluene, 0.132 mmol) was added by syringe or autopipette. The reaction mixture was analyzed by GC and HPLC.

Examples 4–5, 7, 14–17, 24,27, 33 and 34 were carried out as described in Procedure I.

Examples 3, 10, 20–22 and 35 were carried out as described in Procedure II.

Example 1 was carried out as described in Procedure II except the catalyst and ligand were dissolved in 5 ml of benzene, 3.25 mmol of vinyl aromatic compound was used and HCN (0.22M in toluene) was added by syringe pump at 0.5 ml/hr over 16 hours.

Example 2 was carried out as described in Procedure II except the catalyst and ligand were dissolved in 5 ml of benzene, 3.25 mmol of vinyl aromatic compound was used and HCN (0.22M in toluene) was added by syringe pump at 0.25 ml/hr over 16 hours.

Example 6 was carried out as described in Procedure I except 1 mmol of vinyl aromatic compound was used and HCN (0.22M in toluene) was added by syringe pump at 0.25 ml/hr over 16 hours.

Example 8 was carried out as described in Procedure I except the solution of $Ni(COD)_2$ and ligand in benzene was concentrated to dryness in vacuo, redissolved in about 1 ml of hexane and then added to a slurry of the vinyl aromatic compound in about 1 ml of hexane. HCN was added (0.123 ml, 0.132 mmol) as a 1.07M solution in toluene.

Example 9 was carried out as described in Procedure I except HCN was added in three 1.200 ml increments and analyzed after each addition. No change in e.e. was observed as the conversion increased.

Examples 11, 12, 19, 25, 26, 29 and 30 were carried out as described in Procedure I except HCN was added (0.123 ml, 0.132 mmol) as a 1.07M solution in toluene.

Examples 13 and 28 were carried out as described in Procedure I except hexane was substituted for benzene and HCN was added (0.123 ml, 0.132 mmol) as a 1.07M solution in toluene.

Example 18 was carried out as described in Procedure II except 0.013 mmol of $Ni(COD)_2$ (0.004 g) and 0.026 mmol of chiral ligand (0.020 g) in 5 ml of benzene were used and 0.236 ml of HCN was added (0.22M in toluene).

Example 23 was carried out as described in Procedure I except 0.033 mmol of the chiral ligand was used.

Example 31 was carried out as described in Procedure I except 0.020 mmol of $Ni(COD)_2$ and 0.030 mmol of chiral ligand were used.

Example 32 was carried out as described in Procedure II except 0.073 mmol of the chiral ligand was used.

Example 36 was carried out as described in Procedure II except 0.618 ml of HCN was added.

Example 37

Enantioselective Hydrocyanation at High Conversion and Low Ni Loading $Ni(COD)_2$ (0.325 ml of a 0.01M solution in benzene, 0.00325 mmol) and the chiral ligand 3 (0.422 ml of a 0.01M solution in benzene, 0.00423 mmol) were combined with 6-methoxy-2-vinylnaphthalene (0.120 g, 0.65 mmol) in hexane as described in Procedure I. A total of 2.065 ml of 1.07M HCN in toluene was added dropwise by autopipette and the resulting reaction mixture was analyzed by GC and HPLC after about 3–4 hours of stirring. Conversion=93%; E.E.= 83%.

Examples 38 to 45

Enantioselective Hydrocyanation with Non-Carbohydrate Chiral Diolphosphorus Ligands A glass vial (4 cc) was charged with [P(O-o-tolyl)-$_3$]$_2$(C$_2$H$_4$)Ni(O) (0.10 g), [(C$_6$H$_5$)$_2$P]$_2$-(R)-(+)-1,1'-binaphtholate (F) (0.08 g), 2-vinylnaphthalene (0.25 g), and toluene (3 cc) under nitrogen atmosphere and sealed with a septum cap. Aliquots of liquid HCN (5 microliters) were added at 30 minute intervals until no further reaction was observed by gas chromatographic analysis. Conversion=75%; E.E.= 9.6%.

Examples 39–45 were carried out as described in Example 38 using the reagent amounts and conditions detailed in Table 3.

Example 46

Hydrocyanation of Styrene

A mixture of 1.5 g (+) Diop (2,3-O-Isopropylidene-2,3 -dihydroxy-1,4-bis(diphenylphosphino)butane, Aldrich Chemical Co.), 300 mg NiI$_2$, 300 mg zinc dust, 2 ml commercial stabilized styrene, and 2 ml acetonitrile was stirred at 80° for 5 hr. then 250 µl HCN/CH$_3$CN (11N) was added overnight by syringe pump. After addition of 2 ml styrene, 1 ml CH$_3$CN and ca. 100 mg zinc dust another 400 µl HCN/CH$_3$CN was added during eight hours. After addition of 4 ml styrene and 100 mg zinc addition of HCN/CH$_3$CN at 50 µl/hr was continued overnight. The mixture was then diluted with 50 ml heptane and 25 ml ether. The mixture was filtered and the filtrate was concentrated to an oil which was diluted with an equal volume of toluene. The VPC analysis indicated that the two isomeric products PhCH(CN)CH$_3$ and PhCH$_2$CH$_2$CN had been formed in approximately equal amounts. The PhCH(CN)CH$_3$ was isolated by preparative VPC as described above to give 120 mg [α]$_D^{25}$+1.1° C5.5% in CD$_3$CN. An e.e. of about 10% is estimated based on the reported [α]$_D^{25}$ value of 10° for the pure isomer. The $^1$H nmr spectrum was as expected for PhCH(CN)CH$_3$. The major product was apparently styrene polymer which hampered the isolation of the nitrile products.

Example 47

Preparation of Optically Pure (S)-(–)2-(6-methoxy-2 -naphthalene)propionitrile

A solution of Ni(COD)$_2$ (0.002 g, 0.0065 mmol) in about 1 ml of benzene was added to a solution of the chiral ligand phenyl 2,3-bis-O-(3,5-bis(trifluoromethyl)phenyl)phosphino-4,6 -O-benzylidene-(α-D-glucopyranoside, 3, (0.011 g, 0.0085 mmol) in about 1 ml of benzene, stirred for 30 minutes and added to the vinyl aromatic compound 6-methoxy-2-vinylnaphthalene (0.120 g, 0.65 mmol). HCN (1.3 ml, 1.0M in toluene, 1.3 mmol) was added by syringe. The reaction mixture was analyzed by GC after 1 hour of stirring, then concentrated to dryness in vacuo and analyzed by HPLC. Conversion=85%; e.e.=78%. The product nitrile was isolated by flash chromatography (silica gel, 1×12 cm column) using 10% diethyl ether/90% hexane as eluent. Isolated yield 86 mg. Recrystallization from about 20 ml of boiling 10% diethyl ether/hexane afforded 65 mg of nitrile with an e.e. of 89%. A second recrystallization from the same solvent mixture afforded 28 mg of nitrile with an e.e.>99% (melting point=99°–100° C. and [α]$_D^{25}$= –28.4°±1.6°, C 0.5 in CHCl$_3$).

Tables

For the following tables and structures, Ph means phenyl, Ac means acetyl, Me means methyl, and Et means ethyl.

TABLE 1

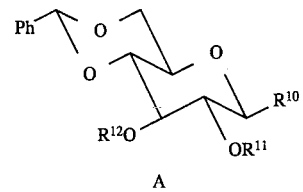

A

Asymmetric Hydrocyanation of 2-Vinylnaphthalene (VN), 6-Methoxy-2-vinylnaphthalene (MVN), 4-Isobutyl-styrene (IBS) or Styrene Using Glucopyranoside Ligand A

| Ex. | R$^{10}$ | R$^{11}$ = R$^{12}$ | L:Ni | Substrate | T (°C.) | Conv. (%) | E.E. (%) |
|---|---|---|---|---|---|---|---|
| 1 | PhO— | Ph$_2$P— | 2:1 | VN | 80 | 43 | 33 |
| 2 | PhO— | Ph$_2$P— | 2:1 | VN | 25 | 3 | 47 |
| 3 | PhO— | Ph$_2$P— | 2:1 | MVN | 25 | 9 | 40 |
| 4 | PhO— | (3-CF$_3$C$_6$H$_4$)$_2$P— | 1.3:1 | VN | 25 | 8 | 71 |
| 5 | PhO— | (3-CF$_3$C$_6$H$_4$)$_2$P— | 1.3:1 | MVN | 25 | 7 | 76 |
| 6 | PhO— | (3-CF$_3$C$_6$H$_4$)$_2$P— | 1.3:1 | MVN | 60 | 23 | 48 |
| 7 | PhO— | (3,5-(CF$_3$)$_2$C$_6$H$_3$)$_2$P— | 1.3:1 | MVN | 20 | 5 | 75 |
| 8 | PhO— | (3,5-(CF$_3$)$_2$C$_6$H$_3$)$_2$P— | 1.3:1 | MVN | 25 | 8 | 83 |
| 9 | PhO— | (3,5-(CF$_3$)$_2$C$_6$H$_3$)$_2$P— | 1.3:1 | VN | 25 | 40 | 78 |
| 10 | PhO— | (EtO)$_2$P— | 2:1 | VN | 25 | 6 | 18 |
| 11 | PhO— | (3,5-(CH$_3$)$_2$C$_6$H$_3$)$_2$P— | 1.3:1 | MVN | 25 | 13 | 16 |
| 12 | PhO— | (3,5-(CH$_3$)$_2$C$_6$H$_3$)$_2$P— | 1.3:1 | VN | 25 | 12 | 25 |
| 13 | PhO— | (3,5-(CH$_3$)$_2$C$_6$H$_3$)$_2$P— | 1.3:1 | VN | 25 | 9 | 43 |

TABLE 1-continued

Structure A: Glucopyranoside ligand with Ph-CH attached via O to a sugar ring bearing substituents $R^{10}$, $OR^{11}$, and $R^{12}O$.

Asymmetric Hydrocyanation of 2-Vinylnaphthalene (VN), 6-Methoxy-2-vinylnaphthalene (MVN), 4-Isobutyl-styrene (IBS) or Styrene Using Glucopyranoside Ligand A

| Ex. | $R^{10}$ | $R^{11} = R^{12}$ | L:Ni | Substrate | T (°C.) | Conv. (%) | E.E. (%) |
|---|---|---|---|---|---|---|---|
| 14 | PhO— | (R)-BINOL phosphite | 1.3:1 | VN | 25 | 2 | 49 |
| 15 | PhO— | (S)-BINOL phosphite | 1.3:1 | VN | 25 | 4 | −13 |
| 16 | PhO— | (S,S)-diphenyl phosphite | 1.3:1 | VN | 25 | 1 | 60 |
| 17 | PhO— | (R,R)-diphenyl phosphite | 1.3:1 | VN | 25 | 1 | 26 |
| 18 | PhCH(CN)O— | $Ph_2P$— | 2:1 | VN | 25 | 3 | 46 |
| 19 | $CH_3O$— | $Ph_2P$— | 1.3:1 | MVN | 25 | 8 | 40 |
| 20 | 2-naphthyl-O— | $Ph_2P$— | 2:1 | VN | 25 | 3 | 52 |
| 21 | 2-naphthyl-O— | $Ph_2P$— | 2:1 | VN | 80 | 1 | 50 |
| 22 | 1-naphthyl-O— | $Ph_2P$— | 2:1 | VN | 25 | 10 | 51 |
| 23 | 2-($Ph_2POCH_2$)phenyl-O— | $Ph_2P$— | 1:1 | VN | 25 | 8 | 45 |

TABLE 1-continued

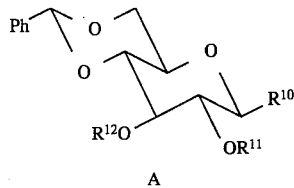

A

Asymmetric Hydrocyanation of 2-Vinylnaphthalene (VN), 6-Methoxy-2-vinylnaphthalene (MVN),
4-Isobutyl-styrene (IBS) or Styrene Using Glucopyranoside Ligand A

| Ex. | $R^{10}$ | $R^{11} = R^{12}$ | L:Ni | Substrate | T (°C.) | Conv. (%) | E.E. (%) |
|---|---|---|---|---|---|---|---|
| 24 | 2-(OSi(Me)$_2$Bu$^t$)-benzyl-O— | Ph$_2$P— | 1.3:1 | VN | 25 | 10 | 49 |
| 25 | (phthalimidomethyl)phenyl-O— | Ph$_2$P— | 1.3:1 | VN | 25 | 7 | 43 |
| 26 | (phthalimidomethyl)phenyl-O— | Ph$_2$P— | 1.3:1 | MVN | 25 | 8 | 36 |
| 27 | 1-adamantyl-O— | (3-CF$_3$C$_6$H$_4$)$_2$P— | 1.3:1 | MVN | 25 | 6 | 22 |
| 28 | PhO— | Ph$_2$P— | 1.3:1 | IBS | 25 | 7 | 10 |
| 29 | PhO— | (3,5-(CF$_3$)$_2$C$_6$H$_3$)$_2$P— | 1.3:1 | IBS | 25 | 9 | −51 |
| 30 | PhO— | (3,5-(CF$_3$)$_2$C$_6$H$_3$)$_2$P— | 1.3:1 | Styrene | 25 | 7 | −10 |

TABLE 2
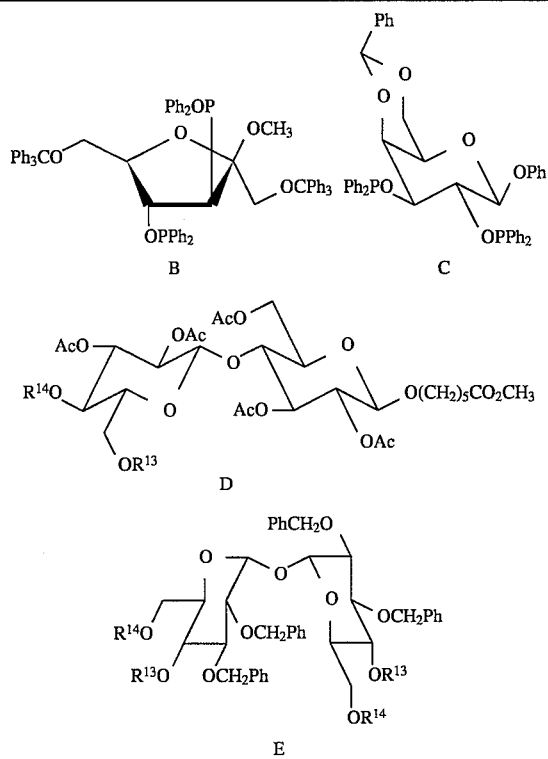
Asymmetric Hydrocyanation Using Ligands (L) B–E
| Ex. | L | $R^{13}$ | $R^{14}$ | L:Ni | Substrate | T (°C.) | Conv. (%) | E.E. |
|---|---|---|---|---|---|---|---|---|
| 31 | B | — | — | 1.5:1 | VN | 25 | 10 | −30 |
| 32 | C | — | — | 2.2:1 | MVN | 25 | 6 | 10 |
| 33 | D | $Ph_2P-$ | $Ph_2P-$ | 1.3:1 | VN | 25 | 11 | −8 |
| 34 | D | $(3\text{-}CF_3C_6H_4)_2P-$ | $(3\text{-}CF_3C_6H_4)_2P-$ | 1.3:1 | MVN | 25 | 13 | −7 |
| 35 | E | $Ph_2P-$ | $PhCH_2O-$ | 2:1 | VN | 25 | 1 | 6 |
| 36 | E | $PhCH_2O-$ | $Ph_2P-$ | 2:1 | MVN | 25 | 10 | 14 |

TABLE 3

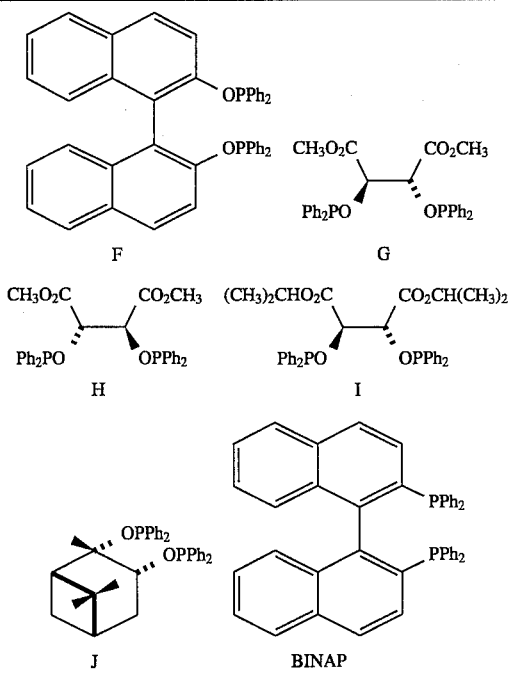

Asymmetric Hydrocyanation of 2-Vinylnaphthalene (VN)
using Non-carbohydrate, Chiral Organophosphorus
Ligands (L), F–J and BINAP

| Ex. | L (mmol) | Ni (mmol) | VN (mmol) | T (°C.) | Conv. (%) | E.E. |
|---|---|---|---|---|---|---|
| 38 | F, .12 | .13 | 1.6 | 25 | 75 | 9.6 |
| 39 | G, .37 | .13 | 1.0 | 75 | >80 | −18 |
| 40 | H, .37 | .13 | 1.0 | 75 | >80 | 18 |
| 41 | H, .55 | .19 | 1.6 | 80 | — | 25 |
| 42 | I, .17 | .063 | .65 | 75 | >90 | −22.4 |
| 43 | J, .37 | .13 | 1.0 | 20 | 7 | 6.4 |
| 44 | (+)BINAP, .14 | .063 | .65 | 20 | >70 | 21.5 |
| 45 | (−)BINAP, .15 | .063 | .65 | 20 | >80 | −21.2 |

We claim:

1. A catalyst composition comprising a source of zero-valent nickel and a chiral, nonracemic, bidentate organophosphorus ligand of the formula

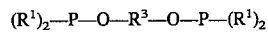

$(R^1)_2$—P—O—$R^3$—O—P—$(R^1)_2$ wherein each $R^1$ is independently a $C_1$ to $C_{20}$ hydrocarbyl, alkoxy or aryloxy, each optionally substituted with one or more alkyl, cycloalkyl, alkenyl, aralkyl, aryl, halogen, ether, ester, carboxy or amide groups; and $R^3$ is a $C_4$ to $C_{40}$ dideoxycarbohydrate, optionally substituted with one or more hydrocarbyl, halogen, ether, ester, alcohol, amide or ketone groups.

2. The composition of claim 1 wherein $R^3$ is a dideoxymonosaccharide, dideoxydisaccharide or dideoxyoligosaccharide.

3. The composition of claim 2 wherein $R^3$ is a dideoxyhexose.

4. The composition of claim 3 wherein $R^3$ is a dideoxyglucose.

5. The composition of claim 3 wherein $R^3$ is a dideoxygalactose.

6. The composition of claim 2 wherein $R^3$ is a dideoxypentose.

7. The composition of claim 2 wherein $R^3$ is a dideoxylactose.

8. The composition of claim 2 wherein $R^3$ is a dideoxytrehalose.

9. The composition of claim 2 wherein $R^3$ is an aryl 2,3-dideoxy 4,6-O-benzylidene β-D-glucopyranoside.

10. The composition of claim 2 wherein $R^3$ is phenyl 2,3-dideoxy-4,6-O-benzylidene β-D-glucopyranoside.

11. The composition of claim 1 wherein $R^1$ is aryl.

12. The composition of claim 11 wherein $R^1$ is phenyl or substituted phenyl.

13. The composition of claim 12 wherein $R^1$ is a halo-substituted phenyl, or a haloalkyl-substituted phenyl.

14. The composition of claim 13 wherein each $R^1$ is 3,5-bis(tri-fluoromethyl)phenyl.

15. The composition of claim 1 wherein the chiral, nonracemic, bidentate organophosphorus ligand is phenyl 2,3-bis-O-(3,5-bis(tri-fluoromethyl phenyl)phosphine-4,6-O-benzilidene-β-D-glucopyranoside.

* * * * *